(12) United States Patent
Friedman et al.

(10) Patent No.: US 8,016,761 B2
(45) Date of Patent: Sep. 13, 2011

(54) METHOD AND APPARATUS FOR AUTOMATED FLOW MEDIATED DILATION

(75) Inventors: Bruce A. Friedman, Tampa, FL (US); Kai E. Thomenius, Clifton Park, NY (US); Aaron M. Dentinger, Latham, NY (US)

(73) Assignee: The General Electric Company, Schenectady, NY (US)

( * ) Notice: Subject to any disclaimer, the term of this patent is extended or adjusted under 35 U.S.C. 154(b) by 1360 days.

(21) Appl. No.: 11/551,749

(22) Filed: Oct. 23, 2006

(65) Prior Publication Data

US 2008/0119743 A1 May 22, 2008

(51) Int. Cl.
*A61B 5/02* (2006.01)
(52) U.S. Cl. .......................... 600/481; 600/485; 600/490
(58) Field of Classification Search .................. 600/490, 600/485, 443–447, 481, 483
See application file for complete search history.

(56) References Cited

U.S. PATENT DOCUMENTS

| | | | | |
|---|---|---|---|---|
| 5,746,698 | A * | 5/1998 | Bos et al. ...................... | 600/493 |
| 6,623,431 | B1 * | 9/2003 | Sakuma et al. ................ | 600/443 |
| 6,654,628 | B1 * | 11/2003 | Silber et al. ................... | 600/410 |
| 6,908,436 | B2 | 6/2005 | Chowienczyk et al. | |
| 2004/0092832 | A1 * | 5/2004 | Schnall et al. ................ | 600/490 |
| 2005/0143640 | A1 | 6/2005 | Hoctor et al. | |
| 2005/0154299 | A1 | 7/2005 | Hoctor et al. | |
| 2005/0228303 | A1 | 10/2005 | Hayano et al. | |
| 2006/0122489 | A1 * | 6/2006 | Kato et al. .................... | 600/411 |
| 2006/0211942 | A1 * | 9/2006 | Hoctor et al. ................. | 600/438 |

FOREIGN PATENT DOCUMENTS

| WO | 03051193 A1 | 6/2003 |
|---|---|---|
| WO | 2005079189 A2 | 10/2006 |

OTHER PUBLICATIONS

"Blood Vessel Endothelial Function Measuring Instrument", Kazuo et al., Patent Abstracts of Japan, Publication No. 200314435.
"Interrelationship between non-invasive measurements of atherosclerosis: flow-mediated dilation of brachial artery, carotid intima-media thickness and pulse wave velocity", Kobayashi et al., aTHEROSCLEROSIS 173 (2004) 13-18.
"Endo-PAT2000—a solution", Itamar Medical Ltd., PN/OM1698602, Aug. 2006.
Endothelix Technology website, www.endothelix.com.

* cited by examiner

*Primary Examiner* — Patricia Mallari
*Assistant Examiner* — Christian Jang
(74) *Attorney, Agent, or Firm* — Andrus, Sceales, Starke & Sawall, LLP

(57) ABSTRACT

A method and system for use in measuring the endothelial dysfunction in a patient utilizing flow mediated dilation. The system includes both a non-invasive blood pressure monitor and an ultrasound system that communicate with each other to perform the flow mediated dilation. Initially, the ultrasound transducer and blood pressure cuff are positioned on an arm of the patient and the blood pressure cuff is inflated to occlude an artery for an occlusion period. Following the occlusion period, the ultrasound system is automatically signaled to begin determining both the diameter of the artery and the flow rate of blood through the artery without any operator intervention. Based upon the detected characteristics of the artery before and after occlusion, the system can determine the endothelial dysfunction of the patient.

18 Claims, 5 Drawing Sheets

METHOD AND APPARATUS FOR AUTOMATED FLOW MEDIATED DILATION

FIELD OF THE INVENTION

The subject matter described herein generally relates to a method and system for the measurement of endothelial dysfunction by flow mediated dilation (FMD). More specifically, the subject matter described herein relates to an automated system for integrating the use of an ultrasound system and an automated NIBP monitor to determine endothelial dysfunction.

BACKGROUND OF THE INVENTION

Endothelial dysfunction is a disruption of the normal biochemical processes carried out by the endothelium, which is a cell group that lines the inner surface of all blood vessels, including arteries and veins. The normal function of the endothelial cells is to produce or release substances that control the biological characteristics of the blood vessels, including the dimension, elasticity, permeability and reactivity. Since impairment of the vascular endothelial function is found in early stages of atherosclerosis, it is possible to treat the atherosclerosis earlier by detecting the impairment of the vascular endothelial function. Endothelial dysfunction is thought to be a key event in the development of atherosclerosis and can predate clinically obvious vascular pathology by many years. Endothelial dysfunction has been shown to be of prognostic significance in predicting vascular events, including stroke and heart attacks.

A key feature of endothelial dysfunction is the inability of the arteries to dilate fully in response to an appropriate stimulus. This can be tested by a variety of methods including intra-arterial administration of various vasoactive agents, localized heating of the skin and temporary arterial occlusion by inflating a blood pressure cuff to high pressures. These techniques are thought to stimulate the endothelium to release nitric oxide (NO) and other agents, which diffuse into the surrounding vascular smooth muscles causing vasodilation. Flow-mediated dilation (FMD) is a non-invasive method for assessing vascular endothelial function by inducing reactive hyperemia with an occlusive cuff and by measuring arterial diameter with an ultrasonic probe. Reactive hyperemia is a transient increase in blood flow that takes place following a brief period of arterial occlusion and the subsequent release thereafter. The flow mediated dilation is a reaction in which an increased arterial blood flow stimulates the vascular endothelium of the artery concerned (typically the brachial artery), thus secreting vascular endothelium-derived relaxing factors that dilate the blood vessels, with a resulting increase in the diameter of the artery. When the vascular endothelial function is impaired the relaxing factors are secreted at a smaller quantity, which results in a smaller increase in arterial diameter. Thus, the vascular endothelial function can be assessed by measuring the extent of the diameter change of the artery following the arterial occlusion and comparing it to reference values Current methods to assess the endothelial function non-invasively use ultrasound to measure the FMD of the limb artery after the release of the temporary occlusion. However, the use of ultrasound probes poses problems for assessment of the vascular endothelial functions. Specifically, in presently used methods, the ultrasound measurements may be poorly reproducible since the technique is highly operator-dependent with regard to the positioning of the probe on the patient. Further, since the prior methods and systems require a trained technician to manually locate the blood vessel within the patient limb and simultaneously integrate the functions of the blood pressure cuff and the ultrasound probe, testing typically takes place in a research environment and is not widely used as a clinical tool.

BRIEF DESCRIPTION OF THE INVENTION

The present disclosure describes a method and system for measuring a characteristic of an artery in a patient to provide an indication of the health of the artery. In one embodiment, a system is provided that includes an ultrasound system and a non-invasive blood pressure (NIBP) monitor that are in communication with each other such that the operation of the ultrasound system and the NIBP monitor can be integrated. Preferably, the non-invasive blood pressure monitor includes a selectively inflatable and deflatable blood pressure cuff that is positioned on a limb of the patient, such as the arm. The ultrasound system includes an ultrasound transducer that is positioned on the same limb of the patient as the blood pressure cuff. Preferably, the blood pressure cuff is positioned distal from the ultrasound transducer.

Once both the ultrasound transducer and the blood pressure cuff are positioned on the patient, the pressure cuff is inflated to a pressure above the patient's systolic pressure to fully occlude the artery for a predetermined period. In one embodiment, the systolic pressure for the patient is determined by the NIBP monitor prior to initiation of the measuring cycle to allow automatic determination of the appropriate occlusion pressure prior to inflation of the pressure cuff for the occlusion period, the ultrasound monitor preferably determines both the diameter of the artery and the blood flow rate through the artery. These measurements are used as baseline values for both the flow rate and diameter.

After the pressure cuff has been inflated for the occlusion period, the NIBP monitor deflates the pressure cuff and communicates the deflation to the ultrasound system. Upon receiving an indication of the deflation of the pressure cuff, the ultrasound system detects characteristics of the artery at regular intervals. Preferably, the ultrasound system determines the diameter of the artery and blood flow rate through the artery at regular intervals following deflation of the pressure cuff. Upon obtaining measurements following deflation of the cuff, the characteristics of the artery can be analyzed. In one embodiment, the characteristics of the artery can be used to determine the endothelial dysfunction for the patient based upon the detected diameter of the artery after the occlusion as compared to the diameter of the artery prior to occlusion.

In one embodiment of the invention, the method and system further includes a heartbeat sensing system that is operable to detect each heartbeat cycle for the patient. Information related to the heartbeat cycle can be relayed to the ultrasound system such that the ultrasound system can obtain measurements at specific points during the heartbeat cycle to enhance the performance of the combined system. In one embodiment, the NIBP monitor, ultrasound monitor and heartbeat sensing system communicate with each other either directly or through a patient monitor such that the determination of the endothelial dysfunction of a patient can be determined automatically without intervention by a technician.

BRIEF DESCRIPTION OF THE DRAWINGS

The drawings illustrate the best mode presently contemplated of carrying out the invention. In the drawings.

DETAILED DESCRIPTION OF THE INVENTION

Figure 1:
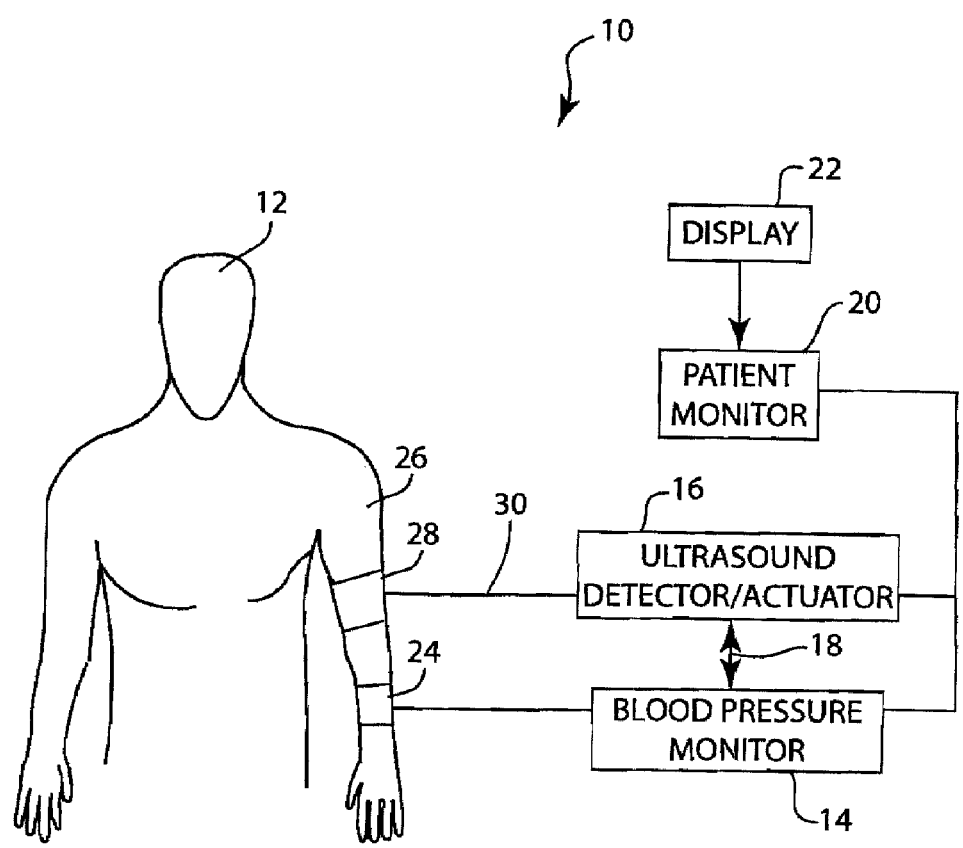
FIG. 1 is a block diagram of a system for measuring endothelial dysfunction by flow mediated dilation using an NIBP monitor and an ultrasound system.

FIG. 1 generally illustrates a system 10 for the automated determination of the endothelial dysfunction of a patient 12 using flow mediated dilation (FMD). The system 10 shown in FIG. 1 preferably includes a non-invasive blood pressure (NIBP) monitor 14 and an ultrasound system 16 that are preferably in direct communication with each other through the communication line 18. In the embodiment shown in FIG. 1, both the ultrasound system 16 and the blood pressure monitor 14 communicate to a patient monitor 20 having a display 22. However, it is contemplated that the patient monitor 20 and display 22 could be eliminated and the blood pressure monitor 14 could communicate directly to the ultrasound system 16 and may include its own internal display to display the measurement of the endothelial dysfunction calculated by the system 10.

In the embodiment shown, the NIBP monitor 10 includes a blood pressure cuff 24 placed on the arm 26 of the patient 12. The blood pressure cuff 24 can be selectively inflated and deflated for occluding an artery of the patient 12 when in the fully inflated condition. In the embodiment shown in FIG. 1, the pressure cuff 24 is shown positioned around the forearm of the patient and is selectively inflatable and deflatable to occlude the radial artery of the patient.

The blood pressure monitor 14 includes both an inflate valve and a deflate valve that are controlled by a central processor to selectively inflate and deflate the pressure cuff 24. The pressure cuff 24 includes a pressure transducer that is used to send pressure oscillations within the cuff 24 that are generated by pressure changes in the artery under the cuff. The electrical oscillation signals from the pressure transducer are obtained by the central processor of the blood pressure monitor 14 and one of several well known algorithms is used to calculate the systolic pressure, mean arterial pressure (MAP) and diastolic pressure for the patient 12.

During normal operation of the NIBP monitor 14, the blood pressure cuff 24 is initially placed on the patient, such as around the subject's lower arm over the radial artery. At the inception of the measuring cycle, the blood pressure cuff 24 is inflated to a pressure that fully occludes the radial artery, thus preventing blood from flowing through the artery at any point in the heart cycle.

After the blood pressure cuff 24 has been inflated to the initial inflation pressure, the deflate valve is actuated by the central processor within the blood pressure monitor 14 to deflate the cuff in a series of pressure steps. At each pressure step, the NIBP monitor 14 detects and records the amplitude of two oscillation pulses for the current cuff pressure level. As the cuff pressure decreases from the initial inflation pressure, the NIBP monitor detects pressure oscillations and records the amplitude for each pressure oscillations for the current cuff pressure. The processor within the blood pressure monitor 14 can then calculate the mean arterial pressure, systolic pressure and diastolic pressure in a known manner.

In addition to the blood pressure monitor 14, the system 10 includes the ultrasound system 16, such as the Vivid I model currently available from GE Healthcare. The ultrasound system 16 generally includes an ultrasound transducer 28 that is also positionable on the arm 26 of the patient 12. In the embodiment shown in FIG. 1, the ultrasound transducer 28 and the pressure cuff 24 are positioned on the same arm of the patient, with the pressure cuff 24 being located distal from the ultrasound transducer 28. In the embodiment shown in FIG. 1, the ultrasound transducer 28 is a low profile ultrasound transducer having one or more sensing elements that can be attached to the patient 12 and is in communication with the ultrasound system 16 through the communication line 30. However, other types of ultrasound transducers are contemplated.

Figure 2:
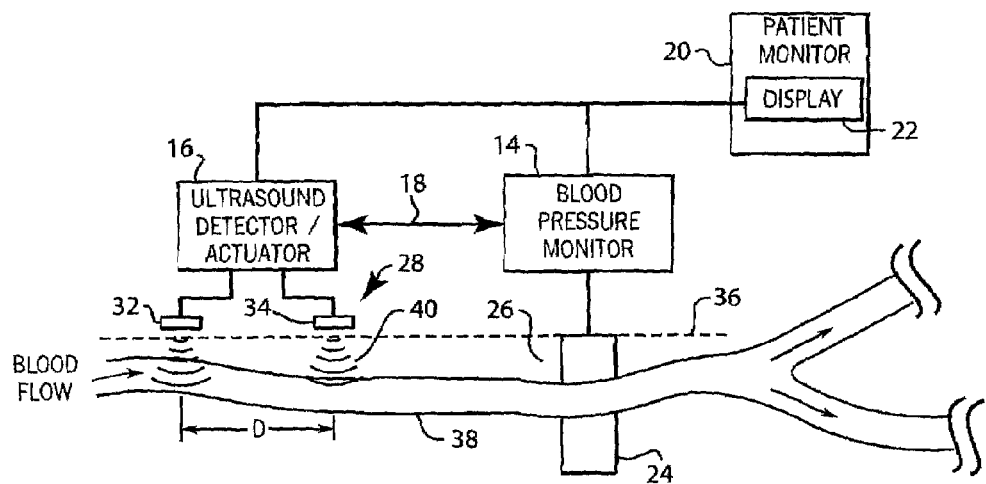
FIG. 2 is a schematic illustration of the interaction between the ultrasound system and blood pressure monitor along an artery of the patient.

Referring now to FIG. 2, the ultrasound transducer 28 is an array transducer including a first ultrasound patch probe 32 and a second patch probe 34 that are positionable on the skin 36 of the patient's arm 26. Although the embodiment of the invention shown in FIG. 2 includes first and second patch probes 32, 34, it should be understood that only a single patch probe or additional patch probes could be utilized while operating within the scope of the present disclosure.

As illustrated in FIG. 2, each of the ultrasound patch probes 32, 34 is positioned on the arm of the patient in such a manner as to enable non-invasive insonification of an artery 38. In the embodiment illustrated, each of the ultrasound patch probes 32, 34 is positioned generally above the brachial artery of the patient. The blood pressure cuff 24 is shown positioned to sense blood pressure in the radial artery of the patient.

Each of the first and second ultrasound patch probes 32, 34 shown in FIG. 2 can be actuated to omit an ultrasound pulse 40. The ultrasound pulse 40 allows the ultrasound system 16 to make multiple measurements and determinations relative to a uniform stretch of an artery, such as the brachial artery 38 positioned beneath each of the ultrasound patch probes 32, 34. In the embodiment of the invention illustrated, the ultrasound patch probe 32, 34 are shown spaced over a length D of the unbifurcated brachial artery.

The processor of the ultrasound system 16 can determine the internal diameter of the artery 38 at the location beneath the first and second ultrasound patch probe 32, 34. In addition to determining the diameter of the artery 38, the processor within the ultrasound system 16 can utilize Doppler ultrasound flow measurement techniques to determine the instantaneous blood velocities beneath the ultrasound transducer 28. Thus, the processor of the ultrasound system 16 can determine both the arterial diameter and blood flow rate at a single location or two separate locations along the brachial artery that are spaced apart by the distance D. These two measurements made through the use of the ultrasound patch probes 32, 34 provide important and accurate information relating to the state of the artery 38.

In the embodiment of the invention illustrated in FIG. 2, each of the ultrasound patch probes 32, 34 has a steerable beam that is operable at an angle with respect to the skin to collect Doppler blood flow measurements. The probes can also be steered to the normal angle and used to measure the area of the arteries lumen. In the embodiment of the invention illustrated, the ultrasound system 16 includes an operating algorithm that allows the ultrasound system 16 to automatically locate and detect the presence of the artery 38 beneath the ultrasound transducer 28. As part of the algorithm to locate and detect the presence of the artery, the ultrasound detector 16 utilizes the patient's heart rate, which is known by the patient monitor 20 as part of the processing technique. Since heart rate demodulation suppresses signals from objects not moving periodically at the heart rate, the use of heart rate demodulation allows the ultrasound detector 16 to detect a vessel containing a pulsating flow of blood and thus locate the vessel within an ultrasound image. In this manner, the ultrasound detector 16 is able to automatically detect the blood vessel once the ultrasound transducer has been placed within a proper range and position on the patient. The algorithm utilized by the ultrasound detector removes the requirement for a trained ultrasonographer to locate the artery and to maintain the position of the transducer relative to the artery.

Figure 3:
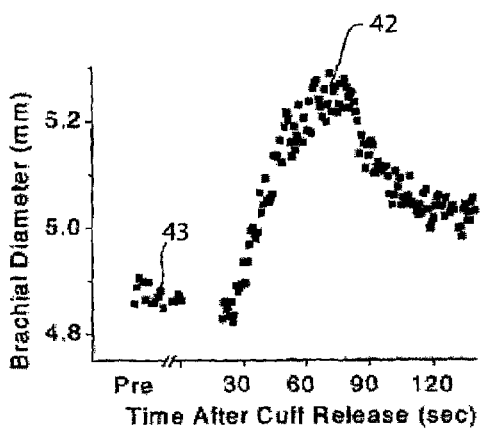
FIG. 3 is a graphic illustrating depicting the diameter of an artery after the temporary arterial occlusion utilizing the blood pressure cuff.

Referring now to FIG. 3, there shown is a representative graph illustrating the response of an artery of a patient following the arterial occlusion by the blood pressure cuff. As illustrated, during normal, steady state, prior to arterial occlusion, the diameter of the artery 43 is approximately 4.9 mm. Following the arterial occlusion for an occlusion period, which is typically approximately 5 minutes, the diameter of the patient artery with normal endothelial function increases to approximately 5.2 mm within one minute after the pressure cuff has been released. Following the maximum dilation 42, the diameter of the artery decreases slowly and returns to near the normal diameter 43 over a period of time. The present FMD is calculated as the percent increase from the steady state pre-occlusion diameter to the maximum diameter post occlusion. The pre-occlusion diameter and maximum diameter measurements taken post occlusion can occur either at the minimum (diastolic) point in the heartbeat cycle, the maximum (systolic) point in the heartbeat cycle, or as an average of the arterial diameter taken over a single cardiac cycle. In any case, the comparison of the arterial diameter prior to occlusion and the diameter post occlusion provides an indication of the arterial health. According to many studies, the percent FMD considered normal is approximately 10% while values in the 3-4% range may be indicative of poor arterial function. Thus, by comparing the normal diameter 44 to the maximum diameter 42, a percent FMD can be calculated to determine the endothelial health of the patient.

Figure 4:
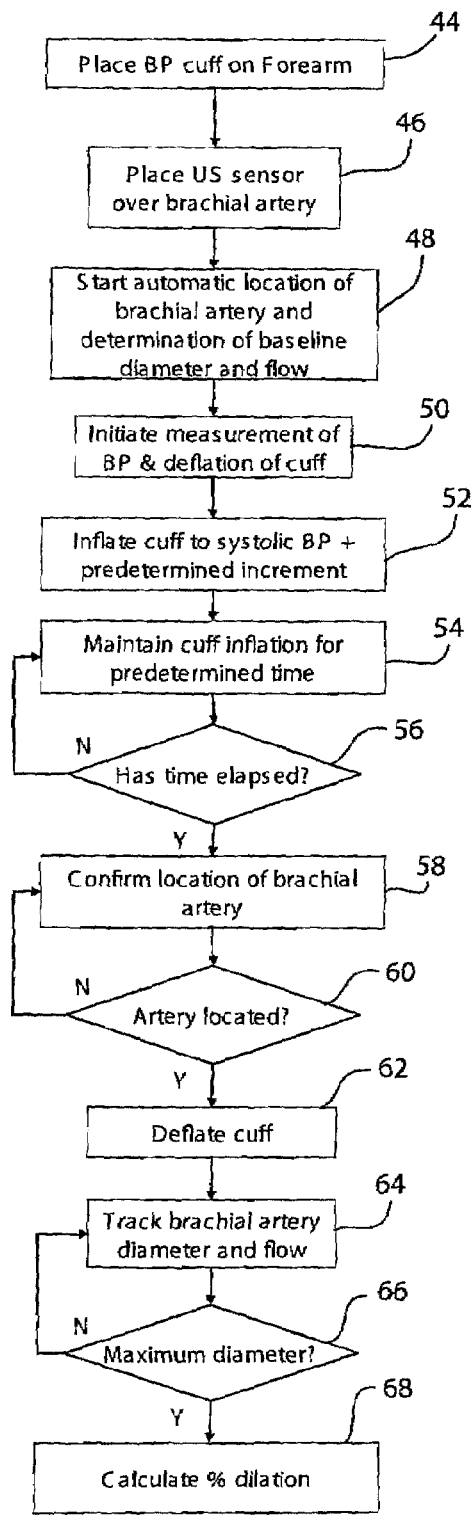
FIG. 4 is a flow chart illustrating the operational sequence utilized by the blood pressure monitor and ultrasound system to measure endothelial dysfunction by flow mediated dilation.

FIG. 4 illustrates a flow chart of the operational sequence between the NIBP monitor and the ultrasound system to determine the endothelial dysfunction in a patient. Initially, in step 44, the blood pressure cuff 24 of the blood pressure monitor 14 is positioned on the forearm of the patient. Once the pressure cuff 24 is properly positioned, the ultrasound transducer 28 is positioned over the brachial artery, as illustrated in step 46. It is contemplated that as the ultrasound actuator 28 is positioned over the upper arm of the patient, the ultrasound transducer 28 will begin emitting an ultrasound beam. When the ultrasound detector 16 detects the presence of the brachial artery beneath the ultrasound transducer 28, the ultrasound detector 16 will signal the technician that the ultrasound transducer is in an acceptable location and that the artery is within view of the ultrasound transducer 28. It is contemplated that the signal to the technician could be an audible indicator, such as a click or beep, or a visual indicator, such as a light or message, to provide positive feedback to the technician that the ultrasound transducer is properly positioned. Once the ultrasound transducer and blood pressure cuff are positioned on the same arm 26 of the patient, the automated process of determining the endothelial dysfunction of the patient can be initiated. Since the ultrasound system 16 and the blood pressure monitor 14 are in communication with each other through the communication line 18, no additional operator input is required for the measurement function after the measurement process has been initiated.

As described previously, the ultrasound system 16 includes an automatic operating algorithm that operates in connection with the one or more patch probes 32, 34 to automatically locate the brachial artery 38 within the patient, as shown in FIG. 2. The automatic location of the brachial artery is carried out by steering or translating the ultrasound beams 40 emitted by each of the patch probes 32, 34 to acquire ultrasound data in a 2-D scan plane or a 3-D scan volume until the processor within the ultrasound system 16 senses the brachial artery. Since the ultrasound system 16 includes an automated algorithm that automatically finds the brachial artery once the ultrasound transducer is positioned in the general vicinity of the artery, skilled operators and/or technicians are not required to initially position the ultrasound probes to detect the brachial artery and ultimately maintain the probe position, which is a vast improvement over prior systems.

Once the ultrasound system automatically locates the brachial artery, the ultrasound system determines a base line diameter and flow rate for the brachial artery in step 48, prior to initiation of the flow mediated dilation scheme.

Once the ultrasound system has made a determination of the base line diameter and flow rate, the ultrasound system signals the blood pressure monitor through the communication line 18 and the blood pressure monitor 14 initiates the measurement of the blood pressure in step 50. Specifically, the blood pressure monitor 14 carries out its normal operating procedure to determine the blood pressure for the patient, which includes inflating the pressure cuff to an initial inflation pressure and decreasing the pressure within the cuff in a series of steps while determining an oscillation amplitude at each step. Based upon the detected oscillation amplitudes, the operating algorithm of the blood pressure monitor 14 calculates at least the systolic blood pressure, mean arterial pressure and diastolic pressure for the patient, which pressures are stored within the blood pressure monitor 14.

After the blood pressure monitor 14 has made an initial blood pressure measurement for the patient, the combined system 10 begins the process of determining the endothelial function for the patient. The first step in monitoring the endothelial function is to inflate the pressure cuff slightly above the systolic blood pressure calculated in step 50. As indicated in step 52, the pressure cuff is inflated to the systolic blood pressure plus a predetermined increment in step 52. In an embodiment of the invention, the increment added to the systolic pressure is approximately 50 mm Hg above the systolic pressure to ensure that the artery is fully occluded.

After inflating the cuff to the occlusion pressure, the cuff is maintained at the occlusion pressure for an occlusion period, as indicated in step 54. Although various occlusion periods can be utilized, in the embodiment of the invention illustrated, the occlusion period is approximately five minutes. The time for the occlusion period can be monitored by either the blood pressure monitor 14 or the ultrasound system 16, since each of these two devices are in communication with each other through the communication line 18.

Once the system determines that the occlusion period has expired in step 56, the blood pressure monitor 14 confirms that the ultrasound system 16 has located the brachial artery beneath the ultrasound transducer in step 58. If the artery has not been located in step 60, the system returns to the step 58 and the ultrasound system 16 continues to attempt to locate the brachial artery. Once the brachial artery has been located, the blood pressure monitor 14 deflates the pressure cuff in step 62. Preferably, the pressure cuff is immediately deflated from the occlusion pressure to well below the diastolic pressure such that blood can flow freely past the pressure cuff immediately upon deflation.

Although the embodiment shown in FIG. 4 contemplates confirming the location of the brachial artery prior to deflation of the pressure cuff in step 62, it is contemplated that the location of the brachial artery could be confirmed after the pressure cuff has been deflated in step 62. Since locating the brachial artery requires detecting either the moving blood or movement of the arterial wall due to a heartbeat, confirming the location of the brachial artery may be more easily carried out once the pressure cuff has been deflated and blood begins to flow in the artery beneath the ultrasound transducer. However, it is contemplated that the system could operate by confirming the location of the brachial artery either prior to or following the deflation of the pressure cuff after the occlusion period.

Following the pressure cuff deflation, the ultrasound system 16 records ultrasound images at the frame rate for the system, which is typically around 30-60 frames per second. Since each frame includes images of the brachial artery diameter and information concerning the blood flow rate, the diameter and flow measurements could be determined from each frame of the ultrasound image. However, it is contemplated that a diameter and flow measurement will be determined only once during each cardiac cycle. As an example, the diameter measurement could be determined at the minimum pressure point (diastolic), maximum pressure point (systolic) or as an average over the entire cardiac cycle. The identification of these points in the cardiac cycle is based upon the timing information related to the duration of the cardiac cycle.

In step 66, either the ultrasound system 16 or the patient monitor 20 can monitor the diameter of the brachial artery and determine whether the diameter measurement has reached a maximum diameter in step 66. As illustrated in FIG. 3, the diameter of the brachial artery increases until the diameter reaches the maximum point 42. Once the diameter reaches the maximum point 42, the diameter of the brachial artery again begins to decrease as the diameter of the brachial artery returns toward the steady state diameter 43. If the ultrasound system determines that the brachial artery has not reached its maximum diameter 42, the ultrasound system 16 continues to monitor the brachial artery diameter and flow in step 64 until the diameter reaches the maximum diameter 42.

Once the maximum diameter has been reached in step 66, either the patient monitor 20 or the ultrasound system 16 calculates a percent dilation in step 68. As indicated previously, the percent FMD relates the steady state diameter 43 to the maximum diameter 42 shown in FIG. 3. Typically, about 10% FMD is considered normal, while 3-4% is abnormal and a variation of as high as 2-3% poses a serious risk. Once the system calculates the percent FMD in step 68, this percent can be shown on the display 22 of the patient monitor 20 and/or stored in the electronic record for the patient.

Although the diameter of the brachial artery is described as being one method of determining endothelial dysfunction, it is contemplated that the flow rate of blood through the brachial artery can also be utilized to determine the endothelial dysfunction for a patient. In such an alternate method of operation, the flow rate of blood through the brachial artery is determined prior to occlusion and compared to the flow rate of blood through the same artery following the occlusion of the artery for the occlusion period. The increase in the flow rate following the occlusion period as compared to the flow rate prior to occlusion is a measure of the flow mediated dilation of the patient's artery.

As can be clearly understood by the above description, the entire process and system for measuring the endothelial dysfunction of a patient is automated and the functions of the blood pressure monitor 14 and ultrasound system 16 are automatically coordinated with each other. Further, the operation of the ultrasound system 16 allows for the automatic detection and location of the brachial artery and thus does not require skilled and trained personnel to perform the ultrasound probe operation.

Figure 5:
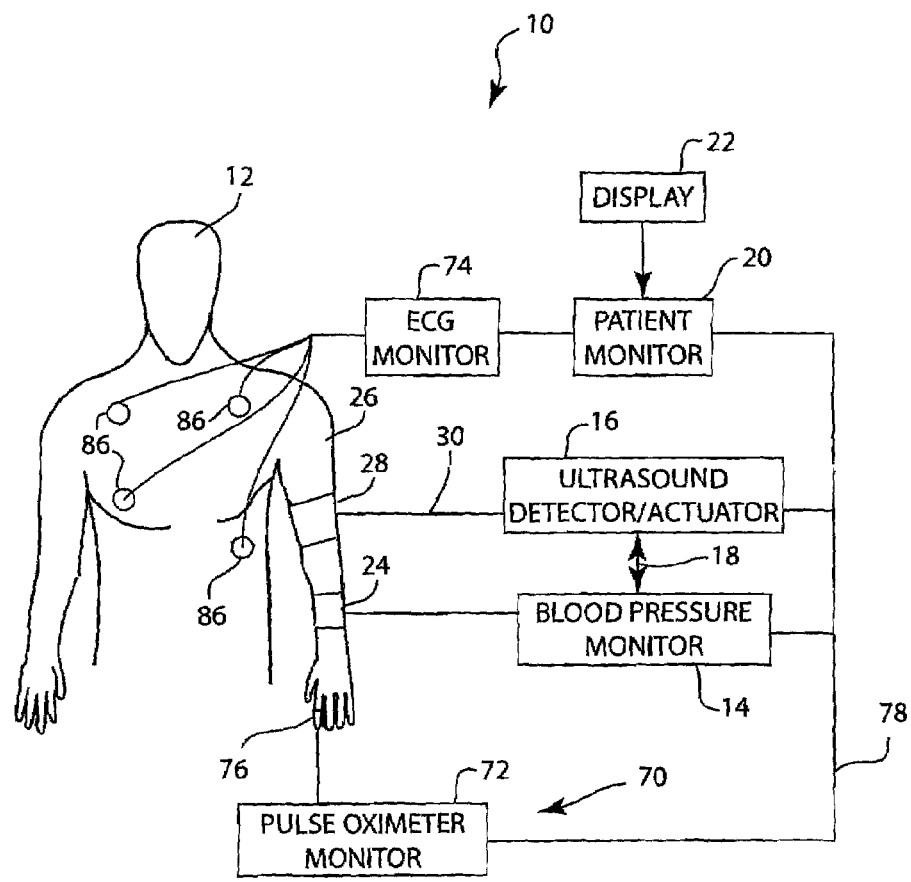
FIG. 5 is a block diagram similar to FIG. 1 illustrating the use of either a pulse oximeter monitor or an ECG monitor to enhance the measurement of endothelial dysfunction by flow mediated dilation.

Referring now to FIG. 5, there shown is an alternate embodiment of the system 10 for determining the endothelial dysfunction in a patient using flow mediated dilation. In the embodiment shown in FIG. 5, similar reference numerals are used for the same operating components included in the first embodiments shown in FIG. 1. In the system shown in FIG. 5, the system includes a heartbeat sensing system 70 that is operable to detect the heartbeat cycles for each heartbeat of the patient 12. In the embodiment shown in FIG. 5, the heartbeat sensing system can be either a pulse oximeter monitor 72 or an ECG monitor 74. As illustrated, both the pulse oximeter monitor 72 and the ECG monitor 74 are connected to the patient monitor 20 and provide signals indicating the timing of the individual patient heartbeat. The information relating to each of the patient's heartbeats is relayed to the patient monitor 20 over a communications line 78 and is used by the ultrasound system 16 to time the measurement of the artery diameter and blood flow rate in a manner to be described in much greater detail below.

Figure 6:
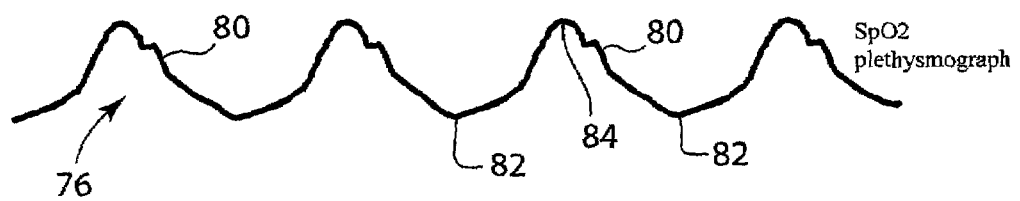
FIG. 6 is an illustration of the plethysmographic waveform received from the pulse oximeter monitor.

As illustrated in FIG. 5, the pulse oximeter monitor 72 includes a finger probe 76 that is positioned on the patient 16 distal from both the pressure cuff 24 and the ultrasound transducer 28. A sensor included within the finger probe 76 determines the $SpO_2$ values for the patient 16 and generates a $SpO_2$ plethysmograph signal 76 (FIG. 6) that is provided to the patient monitor 20 through the communication line 78. As illustrated in FIG. 6, the plethysmograph waveform 76 includes a series of time-spaced pulses 80 that each result from a beat of the patient's heart. Since the finger probe 76 is attached to the patient 12, the pulse oximeter monitoring system 72 continuously monitors the patient and generates a continuous plethysmographic waveform 76 having the series of spaced pulses 80.

As illustrated in FIG. 6, each pulse 80 within the waveform 76 includes a diastolic point 82 and a systolic peak 84. The diastolic point 82 represents the point in the heartbeat cycle for the patient at which the pressure within the artery is the lowest. It has been determined that the diastolic point 82 is the preferred time during the heartbeat cycle to obtain a diameter measurement for the artery. However, it is contemplated by the inventors that various other points during the heartbeat cycle, such as the systolic peak 84, could be utilized. In addition, it is also contemplated that the arterial diameter and flow rates could be averaged over the entire heartbeat cycle while operating within the scope of the present invention.

Referring back to FIG. 5, the ECG monitor 74 includes a series of electrodes 86 positionable on the patient 12. The ECG monitor 74 detects the electrical activity associated with each patient heartbeat and relays this information to the patient monitor 20. Typically, the electrical activity associated with a patient's heartbeat leads the pressure waveforms that are detected by the pulse oximeter monitor 72. Therefore, the patient monitor 20 interprets the signals from the ECG monitor 74 to provide timing signals to the ultrasound system 16. The lead times from the ECG monitor 74 are calculated by the patient monitor 20 in combination with the information received from the ultrasound system 16. The proper offset can be determined by the patient monitor 20 such that the ultrasound system 16 preferably calculates the arterial diameter during the diastolic period of the patient heartbeat cycle. However, other periods of the heartbeat cycle are also contemplated.

Figure 7:
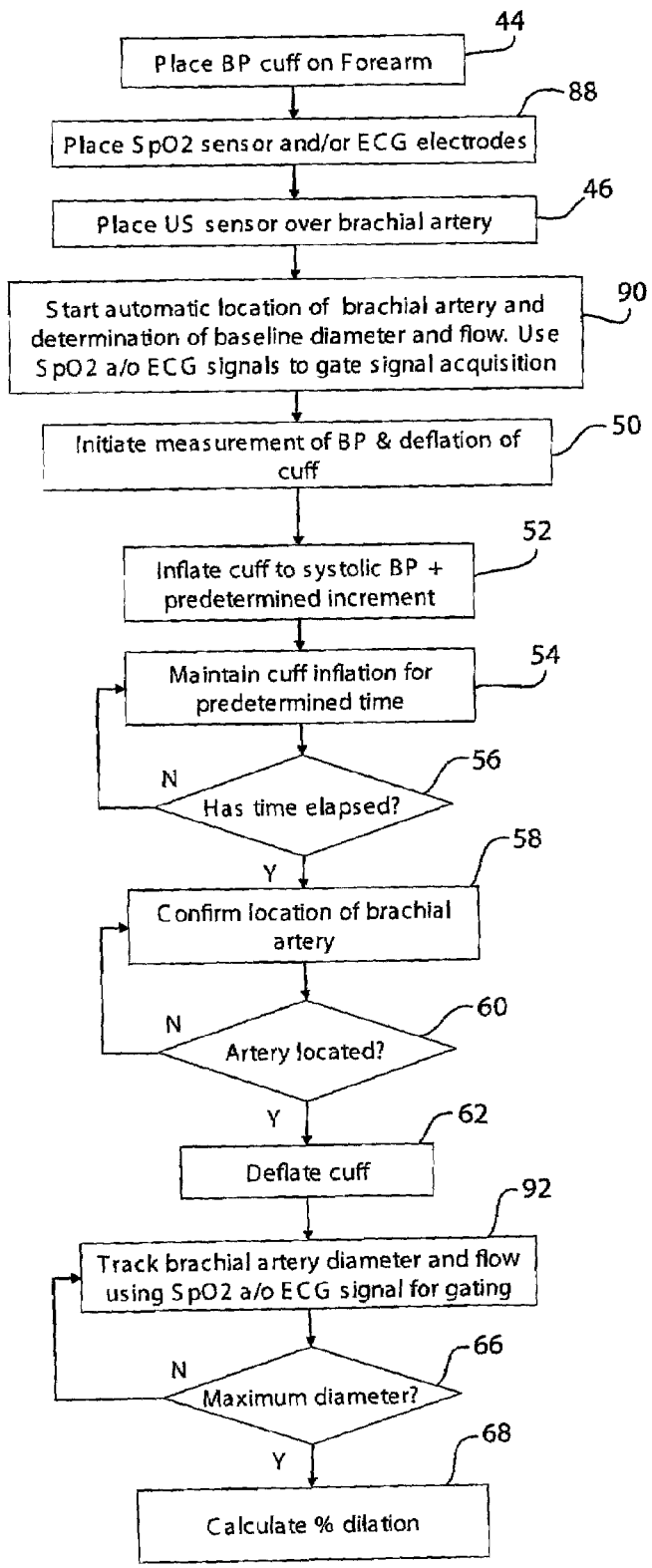
FIG. 7 is a flow chart illustrating the operation sequence for the measurement of endothelial dysfunction incorporating the use of the pulse oximeter monitor and the ECG monitor.

FIG. 7 illustrates a flow chart for the operation of the system shown in FIG. 5, with similar operational steps having the same reference numerals as the first embodiment shown in FIG. 4.

As illustrated in FIG. 7, after the blood pressure cuff has been placed on the forearm in step 44, the SpO$_2$ sensor and ECG electrodes are positioned in step 88. In the embodiment shown in FIG. 5, the SpO$_2$ sensor is part of the finger probe 76 and can be positioned on either the same arm as the pressure cuff 24 or on the opposite arm of the patient 12. If the finger probe 76 is positioned on the same arm as the pressure cuff 24, when the pressure cuff 24 is inflated to the occlusion pressure, the flow of blood past the pressure cuff 24 is terminated such that the SpO$_2$ sensor will not generate the series of SpO$_2$ pulses shown in FIG. 6. However, once the pressure cuff 24 has been deflated below the systolic pressure, the finger probe 76 will again sense the SpO$_2$ pulses 80 shown in FIG. 6.

After placing the SpO$_2$ sensors and/or the ECG electrodes in step 88, the ultrasound transducer 28 is positioned over the brachial artery in step 46. In step 90, the ultrasound system 16 utilizes the signals from either the pulse oximeter monitor 72 or the ECG monitor 74 as a gate signal that identifies the diastolic point during each patient heartbeat. Since the diastolic point has been determined as the most desirable time during a heartbeat cycle to obtain an artery diameter measurement, the ultrasound system 16 collates the ultrasound measurements with the diastolic point in the heartbeat cycle.

As a comparison between FIGS. 4 and 7 indicates, the remaining portions of the operational sequence remain the same until the ultrasound system begins to track the brachial artery diameter and blood flow in step 92. In step 92, the ultrasound system 16 utilizes the timing signals from either the pulse oximeter monitor 72 or the ECG monitor 74 to provide a gating signal such that the artery diameter measurements are taken preferably at the diastolic point of each patient heartbeat. Based upon these timing signals, the ultrasound system 16 can make a more accurate measurement of the artery diameter. Following step 92, the remaining portions of the operational sequence generally correspond to the embodiment shown in FIG. 4 and previously described.

We claim:

1. A method of measuring a characteristic of an artery in a patient, the method comprising the steps of:
   providing an ultrasound system having an ultrasound transducer;
   providing a non-invasive blood pressure (NIBP) monitor having a selectively inflatable and deflatable pressure cuff, the NIBP monitor being in communication with the ultrasound system;
   positioning the ultrasound transducer and the pressure cuff on the patient, the pressure cuff being located distal to the ultrasound transducer;
   automatically inflating the pressure cuff above a systolic pressure for the patient to occlude the artery for an occlusion period;
   operating the ultrasound system to automatically locate the artery beneath the ultrasound transducer;
   confirming the successful location of the artery to the NIBP monitor;
   automatically completely deflating the pressure cuff after the occlusion period and only after receiving confirmation of the successful location of the artery and electronically communicating the deflation to the ultrasound system; and
   automatically operating the ultrasound system to detect the characteristic of the artery below the ultrasound transducer upon notification of the pressure cuff deflation.

2. The method of claim 1 wherein the ultrasound transducer is a linear array having multiple sensing elements.

3. The method of claim 1 further comprising the steps of:
   operating the NIBP monitor to determine at least the systolic pressure for the patient prior to the occlusion period; and
   inflating the pressure cuff to an occlusion pressure greater than the systolic pressure.

4. The method of claim 1 wherein the characteristic of the artery is a diameter of the artery, further comprising the steps of:
   automatically locating the artery beneath the ultrasound transducer and determining the diameter of the artery prior to inflation of the pressure cuff for the occlusion period; and
   comparing the diameter of the artery after the occlusion period to the diameter of the artery before the occlusion period to determine a percentage of dilation.

5. The method of claim 4 further comprising the steps of:
   obtaining multiple diameter measurements for the artery following the deflation of the pressure cuff; and
   automatically calculating the percentage of dilation based upon the maximum diameter detected.

6. The method of claim 1 wherein the characteristic of the artery is a blood flow through the artery.

7. A method of measuring endothelial dysfunction in a patient, the method comprising the steps of:
   providing an ultrasound system having an ultrasound transducer;
   providing a non-invasive blood pressure (NIBP) monitor having a selectively inflatable and deflatable pressure cuff, the NIBP monitor being in communication with the ultrasound system;
   providing a heartbeat sensing system in communication with the ultrasound system and operable to detect each heartbeat cycle for the patient;
   positioning the ultrasound transducer and the pressure cuff on the patient, the pressure cuff being located distal to the ultrasound transducer;
   automatically inflating the pressure cuff above a systolic pressure for the patient to occlude the artery for an occlusion period;
   automatically completely deflating the pressure cuff after the occlusion period and communicating the deflation to the ultrasound system;
   automatically detecting a diameter of an artery below the ultrasound transducer at a detection time within each heartbeat cycle after receiving notification of the pressure cuff deflation; and
   determining the endothelial dysfunction based upon the detected diameters of the artery following the occlusion period.

8. The method of claim 7 wherein the heartbeat sensing system is a pulse oximeter monitor having a pulse oximeter sensor positionable on the patient.

9. The method of claim 7 wherein the heartbeat sensing system is an ECG monitor.

10. The method of claim 7 further comprising the steps of:
operating the ultrasound system to automatically locate the artery beneath the ultrasound transducer;
confirming the successful location of the artery to the NIBP monitor; and
deflating the pressure cuff only after receiving confirmation of the successful location of the artery.

11. The method of claim 10 wherein the ultrasound transducer is a sensor array having multiple sensors.

12. The method of claim 7 further comprising the steps of:
operating the NIBP monitor to determine at least the systolic pressure for the patient prior to the occlusion period; and
inflating the pressure cuff to an occlusion pressure greater than the systolic pressure.

13. The method of claim 12 further comprising the step of confirming the successful location of the artery to the NIBP monitor such that the NIBP monitor automatically deflates the pressure cuff following the occlusion period only upon receiving confirmation of the successful location of the artery.

14. The method of claim 7 wherein the detection time is a diastolic point of the heartbeat cycle as determined by the heartbeat sensing system.

15. A system for the automatic determination of endothelial dysfunction of a patient using flow mediated dilation, comprising:
a non-invasive blood pressure (NIBP) monitor having a pressure cuff positionable on the patient and selectively inflatable and deflatable by the NIBP monitor;
an ultrasound system having an ultrasound transducer positionable on a limb of the patient and operable to determine a diameter of an artery below the ultrasound transducer, and ultrasound system being in communication with the NIBP monitor; and
a heartbeat sensing system positionable on the patient and operable to detect the heartbeat cycles for the patient,
wherein the operation of the ultrasound monitor and the NIBP monitor are communicated to each other to inflate the pressure cuff above a systolic pressure for an occlusion period and to determine a diameter of the artery after deflation of the pressure cuff following the occlusion period at a detection time within each heartbeat cycle as determined by the heartbeat sensing system.

16. The system of claim 15 wherein the heartbeat sensing system is a pulse oximeter monitor.

17. The system of claim 15 wherein the heartbeat sensing system is an ECG monitor.

18. The system of claim 15 wherein the ultrasound transducer is an array of sensors such that the sensor array is automatically operable to detect the artery beneath the ultrasound transducer.

* * * * *